(12) United States Patent
Domeika et al.

(10) Patent No.: US 10,039,503 B2
(45) Date of Patent: Aug. 7, 2018

(54) MONITORING, ANALYSIS, AND FEEDBACK OF ANATOMICAL PRESSURE MEASUREMENTS

(71) Applicant: INTEL CORPORATION, Santa Clara, CA (US)

(72) Inventors: Maximillan J. Domeika, Sherwood, OR (US); Shashi R. Karpur, Chandler, AZ (US); Nina M. Woolvett, Windchester (GB)

(73) Assignee: Intel Corporation, Santa Clara, CA (US)

(*) Notice: Subject to any disclaimer, the term of this patent is extended or adjusted under 35 U.S.C. 154(b) by 0 days.

(21) Appl. No.: 15/282,045

(22) Filed: Sep. 30, 2016

(65) Prior Publication Data

US 2018/0092607 A1 Apr. 5, 2018

(51) Int. Cl.
*A61B 5/00* (2006.01)
*A61B 5/103* (2006.01)
(Continued)

(52) U.S. Cl.
CPC ............ *A61B 5/746* (2013.01); *A61B 5/0022* (2013.01); *A61B 5/103* (2013.01); *A61B 5/6807* (2013.01);
(Continued)

(58) Field of Classification Search
CPC ....... A61B 5/746; A61B 5/0022; A61B 5/103; A61B 5/6807; A61B 5/7282;
(Continued)

(56) References Cited

U.S. PATENT DOCUMENTS

| 7,878,055 B2* | 2/2011 | Balzano | A61B 5/1036 340/573.1 |
| 9,055,925 B2* | 6/2015 | Paquet | A61B 5/6833 |

(Continued)

FOREIGN PATENT DOCUMENTS

WO 2016075523 A1 5/2016

OTHER PUBLICATIONS

International Search Report dated Sep. 29, 2017 for International Patent Application No. PCT/US2017/046326, 3 pages.
(Continued)

*Primary Examiner* — Hai Phan
*Assistant Examiner* — Franklin Balseca
(74) *Attorney, Agent, or Firm* — Finch & Maloney PLLC (57) ABSTRACT

Techniques are provided for monitoring, analysis, and feedback of pressure measurements associated with anatomical regions of a subject user. A methodology implementing the techniques according to an embodiment includes receiving pressure measurement samples from a user-wearable device. The samples are associated with anatomical stress locations of the user, such as, for example, knees, feet, and/or back. The method further includes calculating a percentage of the samples that exceed a threshold pressure value during a selected time period. The method also includes determining an alert condition if the calculated percentage exceeds a percentage threshold value; and generating a notification message based on the alert condition. The notification message is wirelessly transmitted from the user-wearable device to the user's mobile communication device. In some embodiments, the threshold pressure value, selected time period, and percentage threshold value are operational parameters that are wirelessly transmitted from the mobile communication device to the user-wearable device.

19 Claims, 8 Drawing Sheets

(51) Int. Cl.
*A61B 90/00* (2016.01)
*H04L 29/08* (2006.01)
*H04W 4/80* (2018.01)
*H04W 4/00* (2018.01)

(52) U.S. Cl.
CPC ............ *A61B 5/7282* (2013.01); *H04L 67/10* (2013.01); *H04W 4/008* (2013.01); *H04W 4/80* (2018.02); *A61B 2090/065* (2016.02); *A61B 2562/0247* (2013.01)

(58) Field of Classification Search
CPC ..... A61B 2562/0247; A61B 2090/065; H04W 4/008; H04W 4/80; H04L 67/10; H04Q 2209/00; H04Q 2209/80; H04Q 2209/82; H04Q 2209/823
See application file for complete search history.

(56) References Cited

U.S. PATENT DOCUMENTS

| | | | | |
|---|---|---|---|---|
| 2002/0019584 | A1* | 2/2002 | Schulze | G06F 19/3418 600/300 |
| 2009/0024062 | A1 | 1/2009 | Einarsson | |
| 2012/0220835 | A1* | 8/2012 | Chung | A61B 5/0022 600/301 |
| 2012/0253207 | A1* | 10/2012 | Sarkar | G06F 19/3431 600/483 |
| 2014/0277271 | A1 | 9/2014 | Chan et al. | |
| 2014/0378853 | A1* | 12/2014 | McKinney | A61B 5/02438 600/509 |
| 2015/0182182 | A1* | 7/2015 | Tajima | H04N 5/32 378/189 |
| 2016/0066821 | A1 | 3/2016 | Mestrovic et al. | |
| 2016/0067584 | A1* | 3/2016 | Giedwoyn | A61B 5/112 700/91 |
| 2017/0086023 | A1* | 3/2017 | Tartz | H04W 4/023 |

OTHER PUBLICATIONS

Written Opinion dated Sep. 29, 2017 for International Patent Application No. PCT/US2017/046326, 7 pages.

* cited by examiner

FIG. 1

Wearable Device
110

FIG. 8

MONITORING, ANALYSIS, AND FEEDBACK OF ANATOMICAL PRESSURE MEASUREMENTS

BACKGROUND

Stress-related knee injuries can occur when workers are required to perform tasks that involve prolonged periods of time on their knees. Workers, in certain types of jobs, often have no idea how much time they spend on their knees, or when they should take a break. Likewise, management may also be unaware of which jobs are kneeling intensive, and are thus unable to provide guidance or improve task scheduling. The first indication of a problem may often be too late, after injury has occurred. Many other types of stress related injuries are also possible. For example, foot problems may arise from prolonged standing, and back problems can occur after sitting in an uncomfortable position or unsuitable chair for too long.

BRIEF DESCRIPTION OF THE DRAWINGS

Features and advantages of embodiments of the claimed subject matter will become apparent as the following Detailed Description proceeds, and upon reference to the Drawings, wherein like numerals depict like parts.

Although the following Detailed Description will proceed with reference being made to illustrative embodiments, many alternatives, modifications, and variations thereof will be apparent in light of this disclosure.

DETAILED DESCRIPTION

Generally, this disclosure provides techniques for monitoring, analysis, and feedback of pressure measurements associated with anatomical regions of a subject user. Improved monitoring and analysis of force, or pressure, at selected stress locations on the user may allow for early detection and prevention of physical injuries through direct and timely feedback to the user. In some embodiments, a user-wearable device, such as a knee pad, may be equipped with measurement and processing circuitry to collect and analyze pressure measurements, as the user is working or performing some activity. The device circuitry may further be configured to transmit data to a mobile communication platform, such as a smartphone, to provide visual and/or audible notifications and alerts to the user. Additionally, techniques are disclosed to collect such data from the mobile communication platforms of multiple users or workers for transmission to a cloud-based analytics system for further analysis and report generation that may be utilized in worker management decision making and task scheduling.

In accordance with an embodiment, the disclosed techniques can be implemented, for example, in a computing system or a software product executable or otherwise controllable by such systems. The system or product is configured to receive pressure measurement samples from a user-wearable device. The samples are associated with anatomical stress locations of the user, such as, for example, knees, feet, and/or back. The system is further configured to calculate a percentage of the samples that exceed a threshold pressure value during a selected time period, and to generate an alert condition if the calculated percentage exceeds a percentage threshold value. A notification message, based on the alert condition, is also generated and wirelessly transmitted from the user-wearable device to the user's mobile communication device, for example a smartphone. In some embodiments, the threshold pressure value, selected time period, and percentage threshold value are operational parameters that are wirelessly transmitted from the mobile communication device to the user-wearable device.

Figure 1:
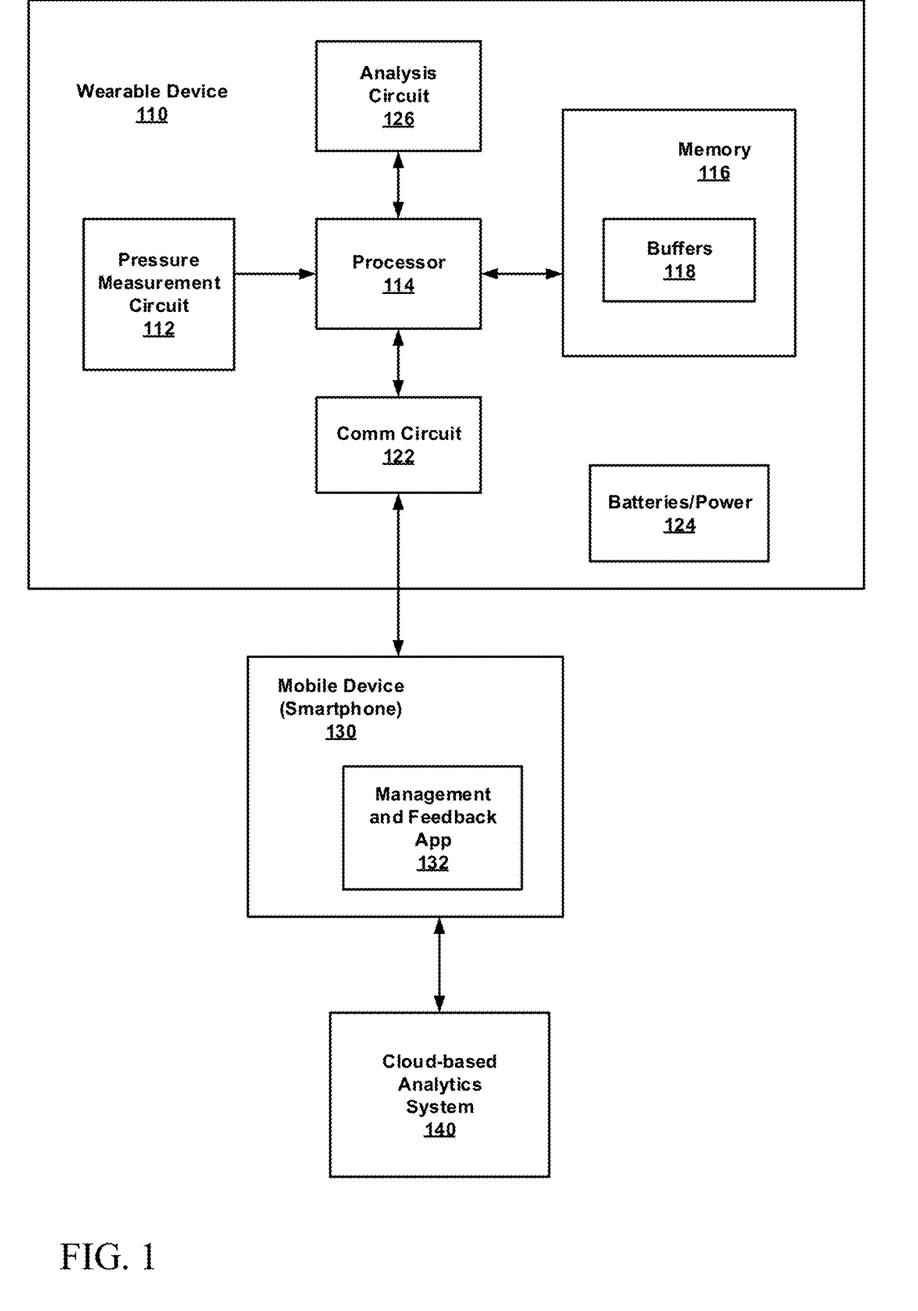
FIG. 1 is a block diagram of an implementation of a system for anatomical pressure management, configured in accordance with certain embodiments of the present disclosure.

The techniques described herein may allow for improved determination of stress conditions, according to an embodiment, by tracking the frequency of occurrence of excessive pressure events during selected time periods, compared to existing techniques that rely on individual pressure measurements which may vary significantly as the worker shifts and moves about. The disclosed techniques can be implemented on a broad range of computing and communication platforms, including wearable devices, such as knee pads, footwear, and back rests, as well as mobile communication devices such as smartphones and the like. These techniques may further be implemented in hardware or software or a combination thereof FIG. 1 is a block diagram 100 of an implementation of a system for anatomical pressure management, configured in accordance with certain embodiments of the present disclosure. A wearable device 110, including pressure measurement and analysis circuitry, is shown to be communicatively coupled to a mobile device 130 (e.g., a smartphone, tablet, etc.). In some embodiments, the wearable device 110 may be a knee pad, footwear (or footwear insert), or a backrest. In a preferred embodiment, the communication between wearable device 110 and mobile device 130 (hereinafter referred to as a smartphone for simplicity), is wireless to facilitate movement and task performance by the user. The wireless communication may conform to a Bluetooth communication protocol. It will be understood, however, that in some embodiments wired communication may also be used. The operations of wearable device 110, and its components, along with smartphone 130 will be described in greater detail below.

Additionally, a cloud-based analytics system 140 is shown, the operations of which will also be described in greater detail below. In some embodiments, smartphone 130 may communicate with system 140 using standard wireless phone communications protocols, in light of the present disclosure.

Wearable device 110 is shown to include a pressure measurement circuit 112, an analysis circuit 126, a processor 114, a memory circuit 116, and a communications circuit 122. In some embodiments, batteries 124, or other suitable power source, are also provided. The pressure measurement circuit 112 is configured to provide pressure measurement samples associated with anatomical stress locations of a subject. The anatomical stress locations may include, for example, one or more of the subject's knees, the subject's feet, and the subject's back. In some embodiments, pressure measurement samples may be obtained from a force sensitive resistor. In some embodiments, the pressure samples may be represented as a data structure that includes, for example, the sensor ID, a timestamp, and a force or pressure measurement, although other representations are possible in light of the present disclosure. The sensor ID can be used indicate the anatomical location of the reading, and the timestamp can be used to subsequently calculate time, frequency and duration statistics, as described below.

The analysis circuit 126 is configured to calculate a percentage of the samples that exceed a threshold pressure value during a selected time period of interest. The analysis circuit 126 is further configured to determine an alert condition when the calculated percentage exceeds a percentage threshold value and to generate a notification message, in response to the determination of the alert condition. The threshold pressure value and the percentage threshold value are selected such that the alert condition will be generated when the worker has exceeded a time critical period in a stressful or unhealthy position (e.g., on their knees). Said differently, the analysis circuit is configured to identify the percentage of time that pressure exceeds a specified threshold for a specified duration. For example, if 80% of the pressure samples collected over the last 15 minutes exceed 75% of the force sensitive resistor threshold, then an alert can be generated. In some embodiments, by considering a combination of both force and time, the system can account for a broader range of situations. For example, if a worker is on both knees, the weight is more distributed and it may be acceptable to be in that position for a longer time period compared to a worked on just one knee.

In some embodiments, the analysis circuit 126 is further configured to maintain statistics associated with frequency of occurrence and durations of the alert condition. These statistics may be used for many purposes, as described below. As one example, the conditions for setting an alert may vary based on the number of prior alerts that have been triggered in a given time period. For instance, after generating 5 alerts, the body may be more irritated and susceptible to injury and thus there may be benefit to relaxing the requirement for alert generation.

In some embodiments, the processor 114 may be configured to coordinate the activities of the circuit components and memory. Additionally, the processor 114 may be configured to assist the analysis circuit 126 by performing some or all of the analysis tasks described above, by executing software comprising instructions stored in memory 116 or other computer readable media. The processor 114 may also monitor other device conditions, such as battery power level, and generate time stamps to be associated with collected data and statistics.

The memory circuit 116 is configured to store the pressure measurement samples for processing by the analysis circuit 126 and/or processor 114. In some embodiments, the samples may be stored in a first-in-first-out (FIFO) buffer, where the latest sample is added and the oldest sample is removed. The size of the FIFO buffer, as well as the pressure measurement sampling rate, may be chosen to match the selected time period so that the FIFO contains a quantity of data that is of interest for each analysis period. In some embodiments, sampling rates may be set at a predetermined value, such as approximately once per second, although this can vary. In some embodiments, the sampling rate may vary, for example to a higher rate when the force values exceed a first threshold or to a lower rate when the force values decrease below a second threshold.

The communications circuit 122 is configured to transmit the notifications to a mobile device over a wireless communications link. Other data may also be transmitted, including the statistics associated with frequency of occurrence and durations of the alert condition, timestamp information, battery power levels, etc. In some embodiments, the wireless communications link comprises Bluetooth communications.

Figure 2:
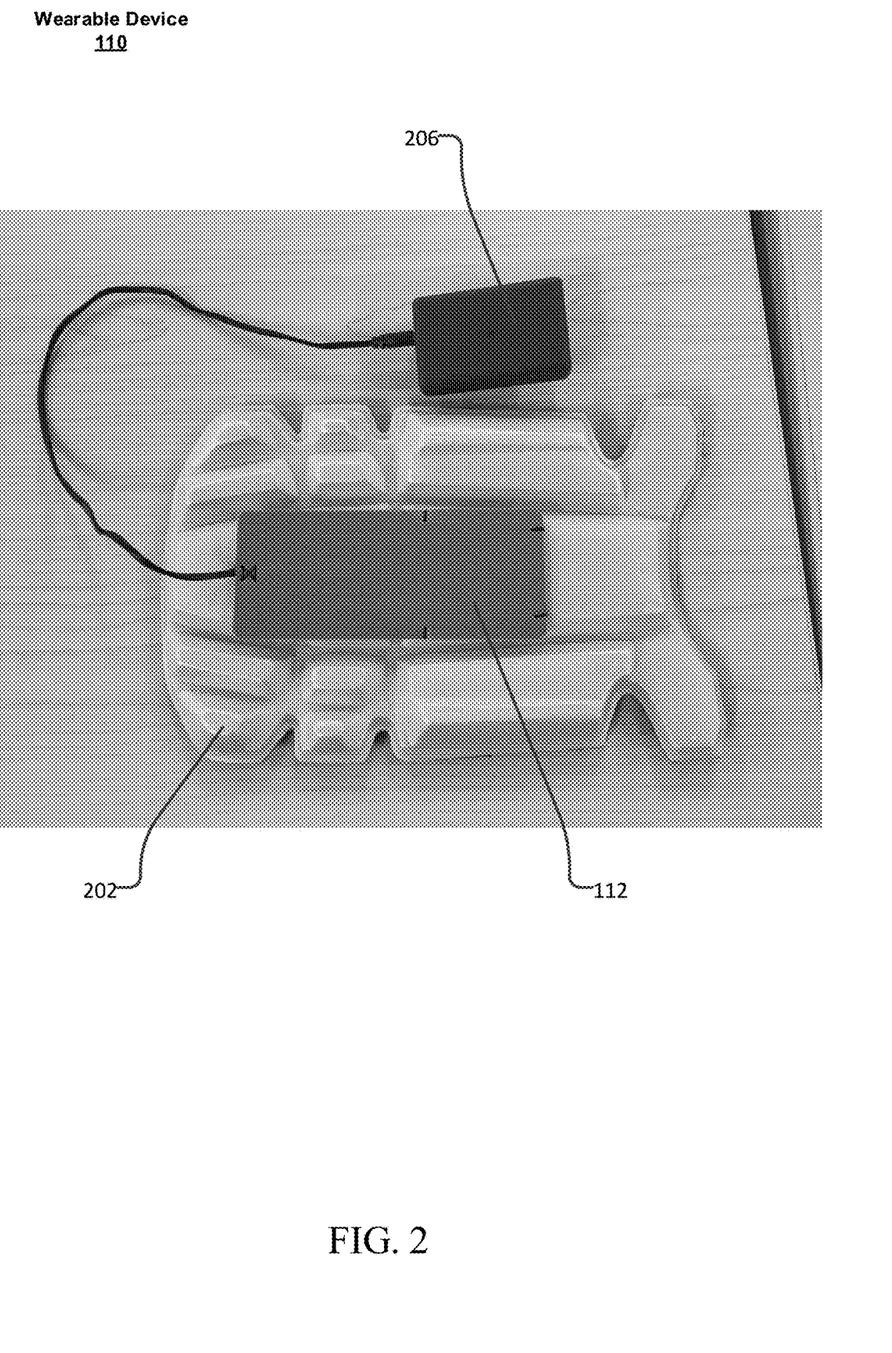
FIG. 2 is an illustration of a user-wearable knee pad device for pressure measurement and analysis, configured in accordance with certain embodiments of the present disclosure.

FIG. 2 is an illustration of a user-wearable knee pad device 110 for pressure measurement and analysis, configured in accordance with certain embodiments of the present disclosure. The user-wearable knee pad device 110 is shown to include the physical knee pad structure 202, which is configured to provide cushioning for the user's knees. Also shown are the pressure measurement circuit 112, which is attached to the underside of the knee pad structure in this illustration, and a circuit board housing 206, configured to contain the other components (processor, memory, analysis circuit, communication circuit, etc.) of the user-wearable device 110.

Figure 3:
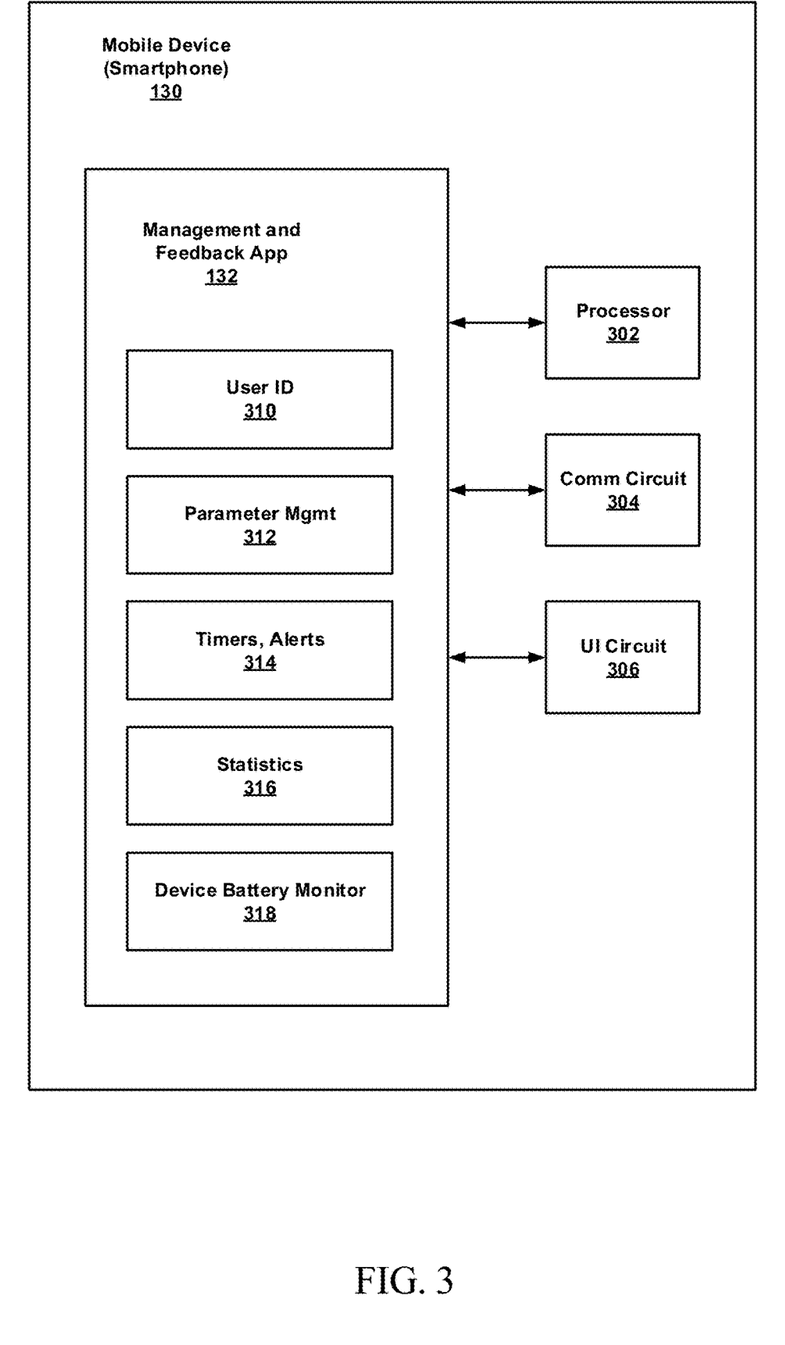
FIG. 3 is a block diagram of a mobile communication device hosting a pressure management and feedback application, configured in accordance with certain embodiments of the present disclosure.

FIG. 3 is a block diagram of a mobile communication device 130 hosting a pressure management and feedback application, configured in accordance with certain embodiments of the present disclosure. The mobile communication device (or smartphone) 130 is shown to include a processor 302, communications circuit 304, and user interface (UI) circuit 306. The processor 302, and/or other components of the smartphone, are configured to host and execute a pressure management and feedback application 132, sometimes referred to as an "App."

The pressure management and feedback application 132 is configured to receive notification messages from the user-wearable device 110. The notification messages are associated with anatomical stress pressure measurements of the user that exceed threshold frequency and duration values. The notification messages may be received through communication circuit 304 and may be wireless communications such as Bluetooth. In response to the notification messages, alerts are generated to the user, for example through UI circuit 306. The alerts may be visual or audible or a combination of both. For example, the alerts may be played through a speaker and/or displayed on a screen of the smartphone. The alerts can indicate to the user that they should take a break, stretch, or exercise. In some embodiments, if the user acknowledges or complies with this suggestion, the alert condition will be cleared and frequency counters and duration timers on the wearable device 110 can be reset, and the FIFO buffer cleared, for detection of subsequent events.

The pressure management and feedback application 132 is further configured to determine the identity (ID) of the user and to transmit the notification messages along with the user ID to a cloud-based analysis system 140. In some embodiments, the ID may be determined through a sign on process or other user interaction through the UI circuit. In other embodiments, the ID may be determined through a facial recognition process utilizing a camera of the smartphone.

The pressure management and feedback application 132 is further configured to determine operational parameters for the user-wearable device 110. These parameters may include, for example, the frequency and duration threshold values that are used to determine alert conditions. In some embodiments, the parameters may be entered by the user, through the UI circuit 306, or may be provided by the cloud-based analysis system 140. The parameters may be wirelessly transmitted through communications circuit 304, for example using Bluetooth.

In some embodiments, the pressure management and feedback application 132 is further configured to receive additional data and statistics from the user-wearable device 110. This additional data may include statistics associated with frequency of occurrence and durations of the alert condition, timestamp information, and battery power levels of the user-wearable device 110. This additional data may also be displayed to the user and/or transmitted to the cloud-based analysis system.

Figure 4:
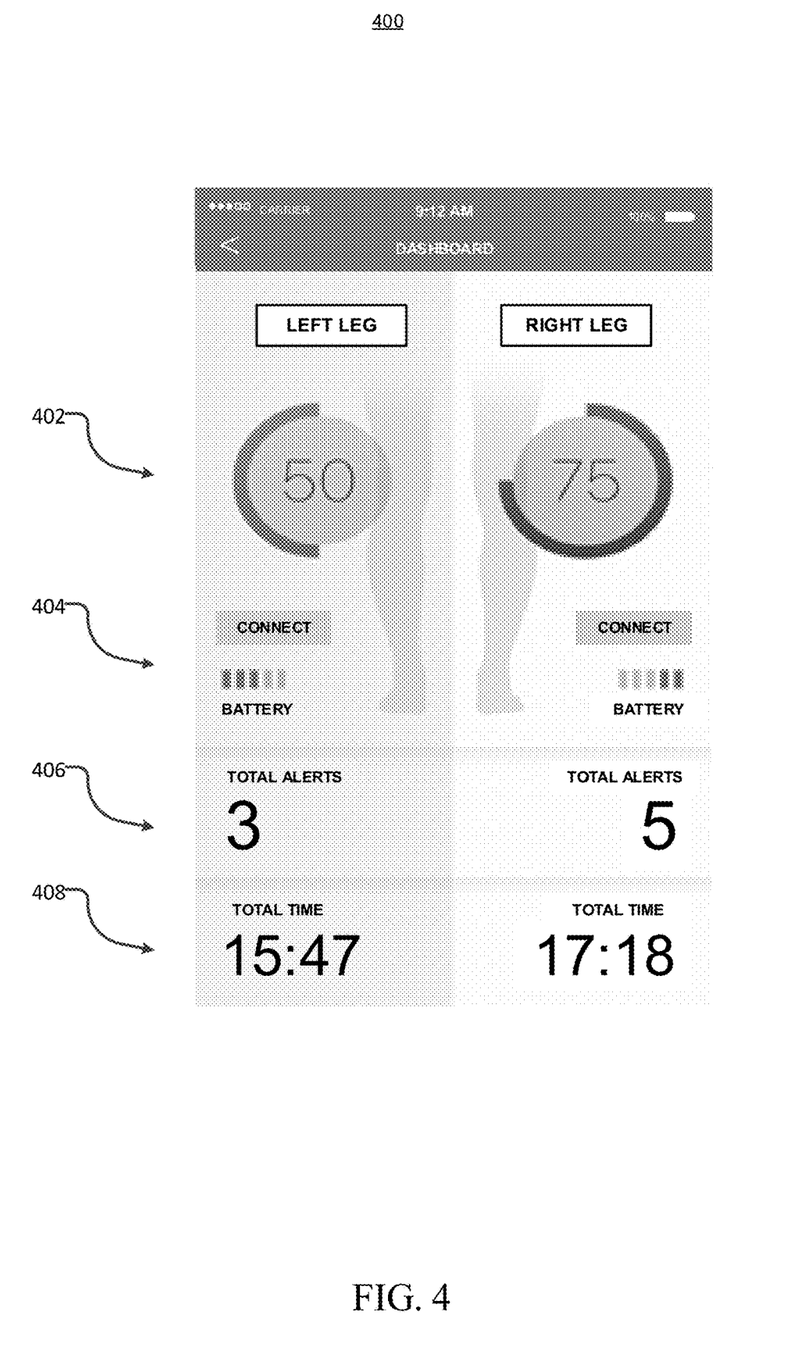
FIG. 4 is an example user interface display on the mobile communication device, configured in accordance with certain embodiments of the present disclosure.

FIG. 4 is an example user interface display 400 on the mobile communication device, configured in accordance with certain embodiments of the present disclosure. The example user interface display 400 is shown to include visual indicators of the stress levels of the user's left and right legs 402. A connection status, between the smartphone and the user-wearable devices, as well as battery power levels are also displayed 404. Additionally, a count of alerts 406 and an indication of the total duration time 408 of excessive stress conditions are provided.

Figure 5:
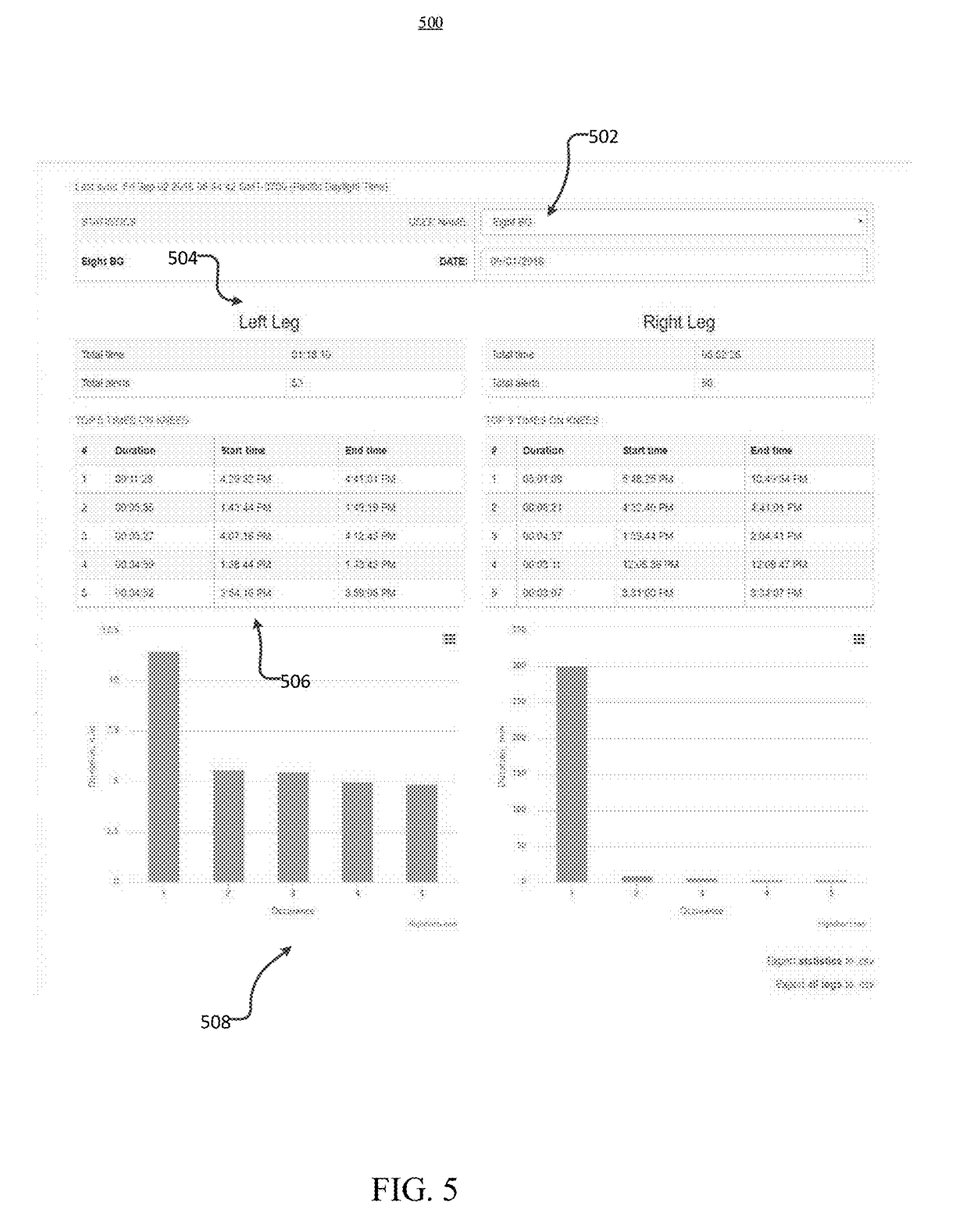
FIG. 5 is an example user interface display on a cloud-based analytics system, configured in accordance with certain embodiments of the present disclosure.

FIG. 5 is an example user interface display 500 on a cloud-based analytics system 140, configured in accordance with certain embodiments of the present disclosure. The cloud-based analytics system 140 may be configured to aggregate data collected from multiple users for further analysis and report generation. The example user interface display 500 is shown to provide, for any selected user 502, statistics on number of alerts and durations for each anatomical location (e.g., left leg and right leg in this example). Many additional display features are, of course, possible, including listings of top N occurrences 506 and bar graphs 508, etc. The aggregated data may be used to assist management in identifying physically stressful jobs and in making decisions regarding worker scheduling, task assignment, and health coaching.

Methodology

Figure 6:
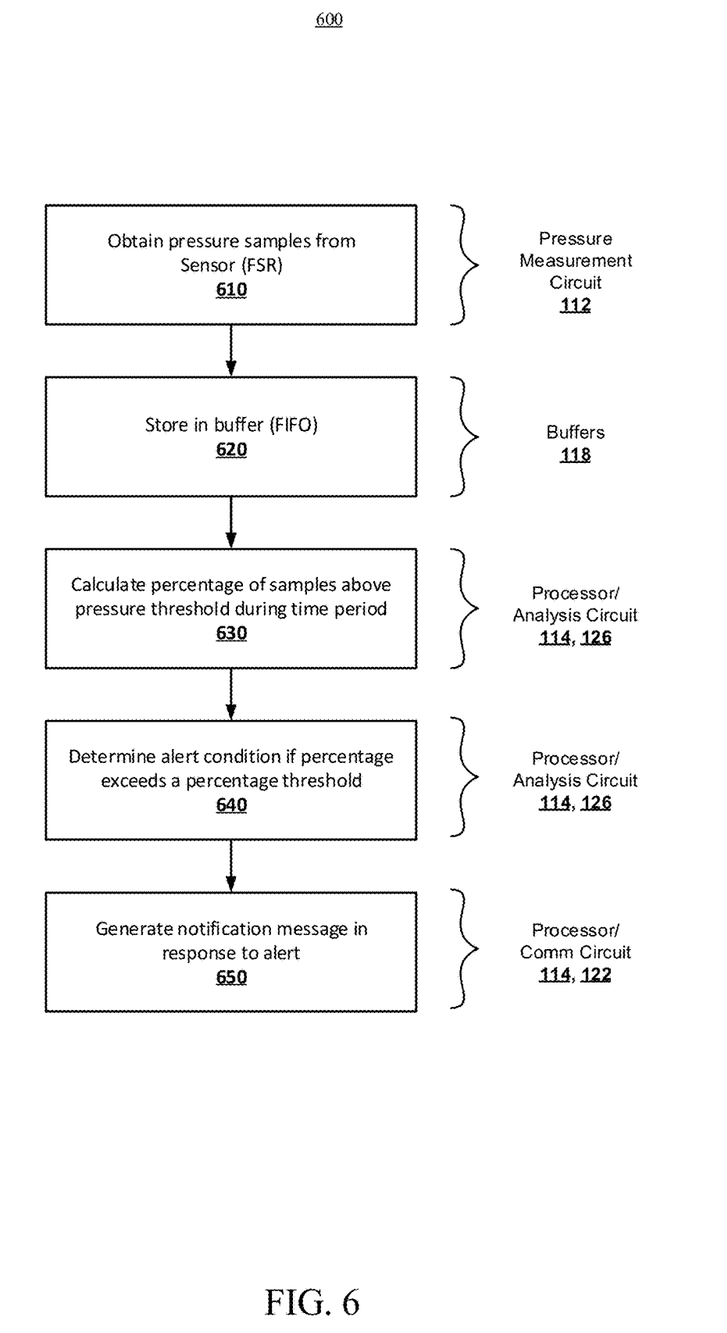
FIG. 6 is a flowchart illustrating a methodology for pressure measurement and analysis on the user-wearable device, in accordance with certain embodiments of the present disclosure.

FIG. 6 is a flowchart illustrating an example method 600 for pressure measurement and analysis on the user-wearable device, in accordance with certain embodiments of the present disclosure. As can be seen, example method 600 includes a number of phases and sub-processes, the sequence of which may vary from one embodiment to another. However, when considered in the aggregate, these phases and sub-processes form a process for pressure measurement and analysis in accordance with certain of the embodiments disclosed herein. These embodiments can be implemented, for example using the system architecture illustrated in FIG. 1 as described above. However other system architectures can be used in other embodiments, as will be apparent in light of this disclosure. To this end, the correlation of the various functions shown in FIG. 6 to the specific components illustrated in the other figures is not intended to imply any structural and/or use limitations. Rather, other embodiments may include, for example, varying degrees of integration wherein multiple functionalities are effectively performed by one system. For example, in an alternative embodiment a single module can be used to perform all of the functions of method 600. Thus other embodiments may have fewer or more modules and/or sub-modules depending on the granularity of implementation. In still other embodiments, the methodology depicted can be implemented as a computer program product including one or more non-transitory machine readable mediums that when executed by one or more processors cause the methodology to be carried out. Numerous variations and alternative configurations will be apparent in light of this disclosure.

As illustrated in FIG. 6, in one embodiment, method 600 for pressure measurement and analysis commences by receiving, at operation 610, pressure measurement samples associated with anatomical stress locations of the subject user. The pressure measurement samples may be generated by a force sensitive resistor. In some embodiments, the anatomical stress locations may include the subject's knees, feet, and/or back.

Next, at operation 620, a calculation is performed to determine the percentage of the samples that exceed a threshold pressure value during a selected time period. At operation 630, an alert condition is generated if the calculated percentage exceeds a percentage threshold value.

At operation 640, a notification message is generated in response to the alert condition. In some embodiments, the notification message may be transmitted wirelessly from the user-wearable device to a mobile communication platform, such as, for example, the user's smart phone. In some embodiments, the wireless communication may be performed using Bluetooth.

Of course, in some embodiments, additional operations may be performed, as previously described in connection with the system. For example, the pressure measurement samples may be stored in a FIFO memory buffer, where the size of the FIFO buffer and the sampling rate for the pressure measurements are chosen to match the selected time period.

Further additional operations may include maintaining statistics associated with frequency of occurrence and durations of the alert condition.

Figure 7:
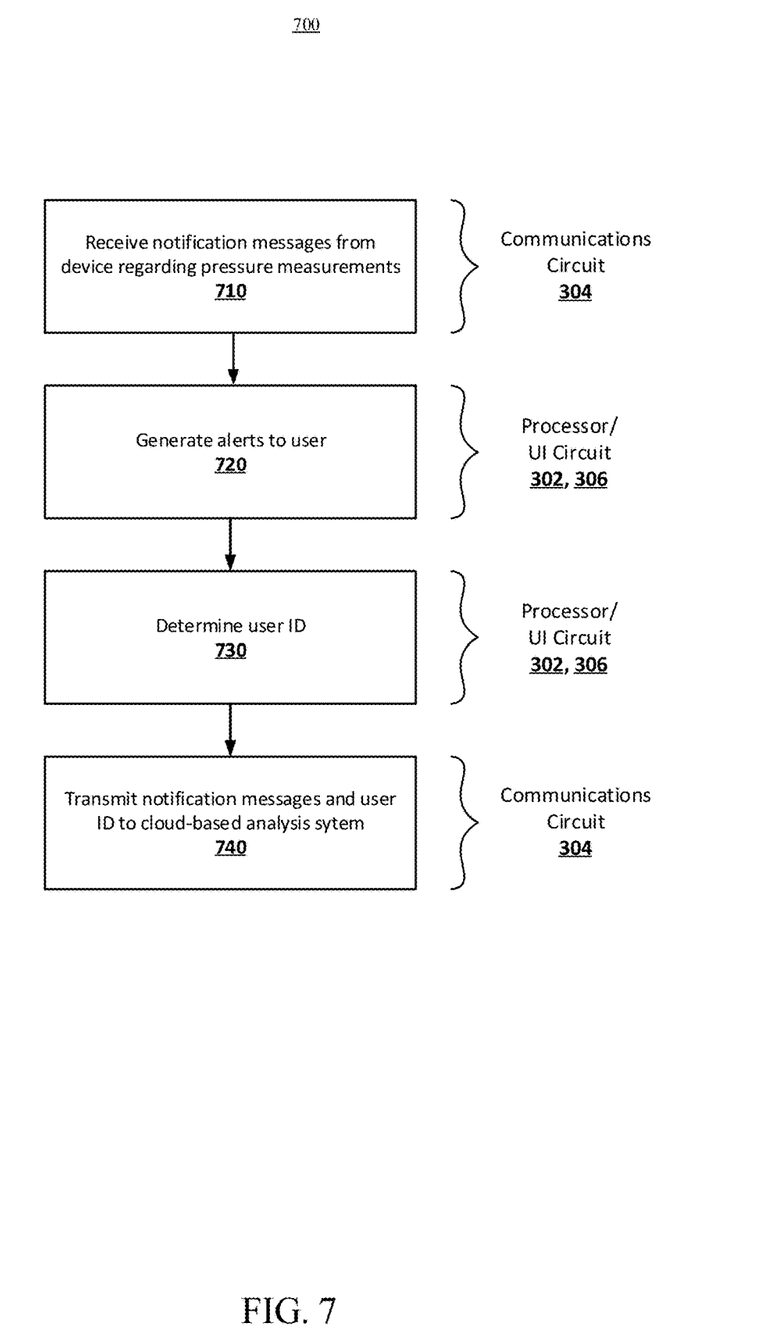
FIG. 7 is a flowchart illustrating a methodology for pressure measurement and analysis on the mobile communication device, in accordance with certain embodiments of the present disclosure.

FIG. 7 is a flowchart illustrating an example method 700 for pressure measurement and analysis on the mobile communication device, in accordance with certain embodiments of the present disclosure. As can be seen, example method 700 includes a number of phases and sub-processes, the sequence of which may vary from one embodiment to another. However, when considered in the aggregate, these phases and sub-processes form a process for pressure measurement and analysis in accordance with certain of the embodiments disclosed herein. These embodiments can be implemented, for example using the system architecture illustrated in FIGS. 1 and 3 as described above. However other system architectures can be used in other embodiments, as will be apparent in light of this disclosure. To this end, the correlation of the various functions shown in FIG. 7 to the specific components illustrated in the other figures is not intended to imply any structural and/or use limitations. Rather, other embodiments may include, for example, varying degrees of integration wherein multiple functionalities are effectively performed by one system. For example, in an alternative embodiment a single module can be used to perform all of the functions of method 700. Thus other embodiments may have fewer or more modules and/or sub-modules depending on the granularity of implementation. In still other embodiments, the methodology depicted can be implemented as a computer program product including one or more non-transitory machine readable mediums that when executed by one or more processors cause the methodology to be carried out. Numerous variations and alternative configurations will be apparent in light of this disclosure.

As illustrated in FIG. 7, in one embodiment, method 700 for pressure measurement and analysis commences by receiving, at operation 710, notification messages from the user-wearable device. The notification messages are associated with alerts generated by the user-wearable device in response to detection of anatomical pressure measurements that exceed a threshold with a given frequency over a selected period of time. In some embodiments, the notification messages may be transmitted wirelessly from the user-wearable device, for example using Bluetooth communications.

Next, at operation 720, alerts are generated and provided to the user, based on the notification messages. In some embodiments, the alerts may be audible and/or visual. For example, the alerts may be played through a speaker and/or displayed on a screen of the mobile communication device.

At operation 730, the identity (ID) of the user of the mobile communication device is determined. In some embodiments, the ID may be determined through a sign on process or other user interface interaction. In other embodiments, the ID may be determined through a facial recognition process utilizing a camera of the mobile communication device.

At operation 740, the notification messages are transmitted to a cloud-based analysis system along with the user ID. In some embodiments, the cloud-based analysis system may aggregate such data collected from multiple users for further analysis and report generation.

Of course, in some embodiments, additional operations may be performed, as previously described in connection with the system. For example, the frequency and duration threshold values may be selected and transmitted to the user-wearable device for use in generating alert conditions. Further additional operations may include receiving statistics associated with the anatomical stress pressure measurements from the user-wearable device, displaying those statistics to the user, and transmitting the statistics to the cloud-based analysis system. For example, metrics such as the top five kneeling duration times along with the total time spent on knees may be useful at the aggregate level. Such information may indicate that a particular population which spent more than X hours on their knees appears to be suffering more injuries than other populations.

Example System

Figure 8:
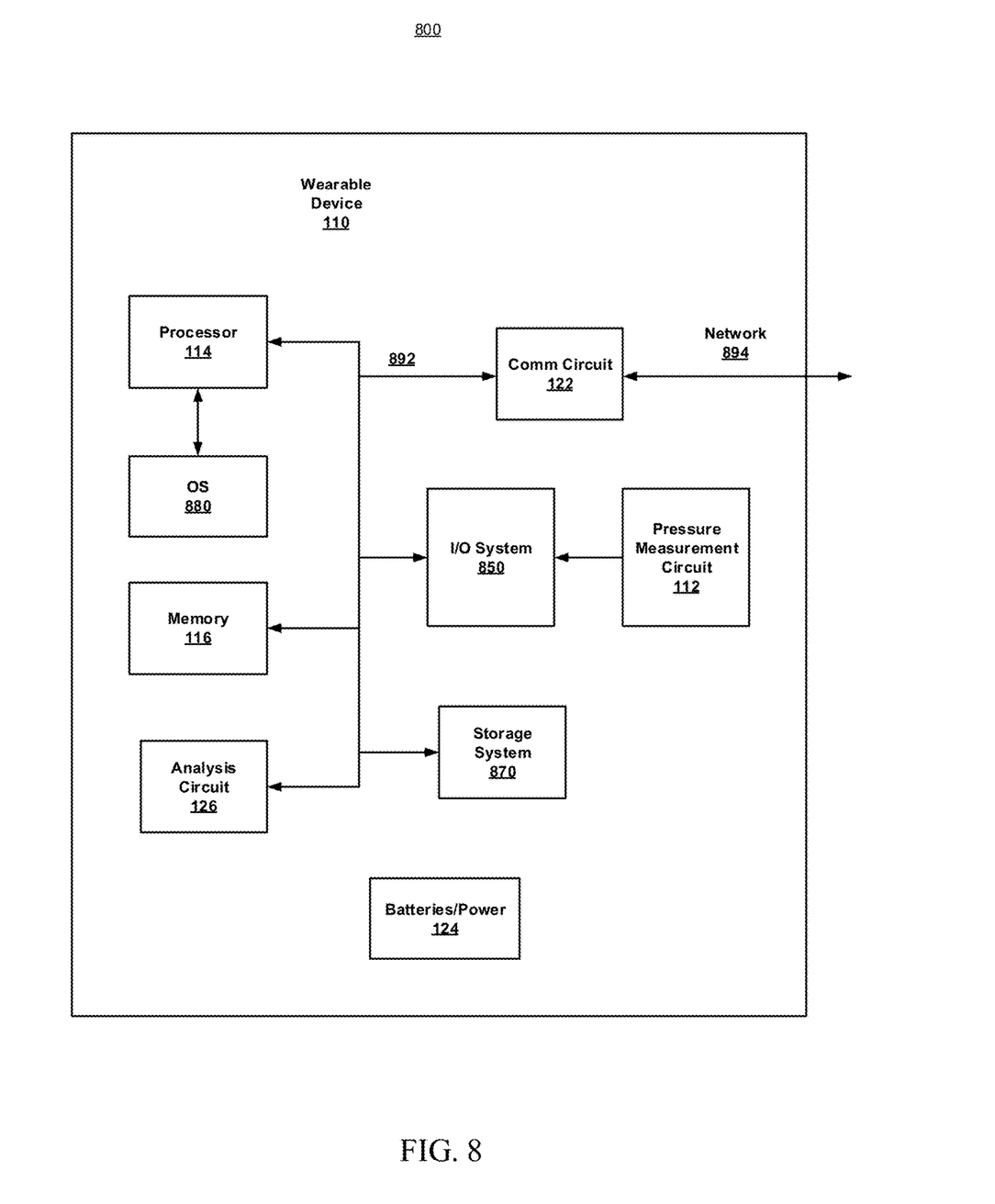
FIG. 8 is a block diagram schematically illustrating a wearable device platform to perform anatomical pressure measurement and analysis, configured in accordance with certain embodiments of the present disclosure.

FIG. 8 illustrates an example system platform 800 to perform monitoring, analysis, and feedback of pressure measurements, configured in accordance with certain embodiments of the present disclosure. The pressure measurements are associated with anatomical regions of a subject user, such as, for example, knees, feet, and back. In some embodiments, system platform 800 may be configured as a wearable device 110 such as, for example, a knee pad, footwear, back rest, etc.

In some embodiments, wearable device 110 may comprise any combination of a processor 114, a memory 116, an analysis circuit 126, a communication circuit 122, an input/output (I/O) system 850, a pressure measurement circuit 112, a storage system 870, and batteries or other power source 124. As can be further seen, a bus and/or interconnect 892 is also provided to allow for communication between the various components listed above and/or other components not shown. Wearable device 110 can be coupled to a network 894, such as, for example, a wireless communication medium, through communication circuit 122 to allow for communications with other computing devices, platforms or resources. In some embodiments, Bluetooth communications may be used to interface to a user's smartphone or similar device. Other componentry and functionality not reflected in the block diagram of FIG. 8 will be apparent in light of this disclosure, and it will be appreciated that other embodiments are not limited to any particular hardware configuration.

Processor 114 can be any suitable processor, and may include one or more coprocessors, controllers, or microcontrollers, to assist in control and processing operations associated with platform 800. In some embodiments, the processor 114 may be implemented as any number of processor cores. The processor (or processor cores) may be any type of processor, such as, for example, a micro-processor, an embedded processor, a digital signal processor (DSP), a graphics processor (GPU), a network processor, a field programmable gate array or other device configured to execute code. The processors may be multithreaded cores in that they may include more than one hardware thread context (or "logical processor") per core. Processor 114 may be implemented as a complex instruction set computer (CISC) or a reduced instruction set computer (RISC) processor. In some embodiments, processor 114 may be configured as an x86 instruction set compatible processor.

Memory 116 can be implemented using any suitable type of digital storage including, for example, flash memory and/or random access memory (RAM). In some embodiments, the memory 116 may include various layers of memory hierarchy and/or memory caches as are known to those of skill in the art. Memory 116 may be implemented as a volatile memory device such as, but not limited to, a RAM, dynamic RAM (DRAM), or static RAM (SRAM) device. Storage system 870 may be implemented as a non-volatile storage device such as, but not limited to, one or more of a hard disk drive (HDD), a solid state drive (SSD), a universal serial bus (USB) drive, an optical disk drive, tape drive, an internal storage device, an attached storage device, flash memory, battery backed-up synchronous DRAM (SDRAM), and/or a network accessible storage device. In some embodiments, storage 870 may comprise technology to increase the storage performance enhanced protection for valuable digital media when multiple hard drives are included.

Processor 114 may be configured to execute an Operating System (OS) 880 which may comprise any suitable operating system, such as Google Android (Google Inc., Mountain View, Calif.), Microsoft Windows (Microsoft Corp., Redmond, Wash.), Apple OS X (Apple Inc., Cupertino, Calif.), or a real-time operating system. As will be appreciated in light of this disclosure, the techniques provided herein can be implemented without regard to the particular operating system provided in conjunction with platform 800, and therefore may also be implemented using any suitable existing or subsequently-developed platform.

Communications circuit 122 can be any appropriate network chip or chipset which allows for wired and/or wireless connection between other components of platform 800 and/or network 894, thereby enabling platform 800 to communicate with other local and/or remote computing systems, servers, and/or resources. Wired communication may conform to existing (or yet to developed) standards, such as, for example, Ethernet. Wireless communication may conform to existing (or yet to developed) standards, such as, for example, cellular communications including LTE (Long Term Evolution), Wireless Fidelity (Wi-Fi), Bluetooth, and/or Near Field Communication (NFC). Exemplary wireless networks include, but are not limited to, wireless local area networks, wireless personal area networks, wireless metropolitan area networks, cellular networks, and satellite networks.

I/O system 850 may be configured to interface between various I/O devices and other components of platform 800, including pressure measurement circuit 112. I/O devices may also include, but not be limited to, a user interface and test port, not shown.

It will be appreciated that in some embodiments, the various components of the platform 800 may be combined or integrated in a system-on-a-chip (SoC) architecture. In some embodiments, the components may be hardware components, firmware components, software components or any suitable combination of hardware, firmware or software.

Analysis circuit 126 is configured to perform monitoring, analysis, and feedback of pressure measurements associated with anatomical regions of the subject user. The pressure measurement may be provided by pressure measurement circuit 112, which in some embodiments may be implemented as a force sensitive resistor. Analysis circuit 126 may include any or all of the components illustrated in FIG. 1, as described above. Analysis circuit 126 can be implemented or otherwise used in conjunction with a variety of suitable software and/or hardware that is coupled to or that otherwise forms a part of wearable device 110. Analysis circuit 126 can additionally or alternatively be implemented or otherwise used in conjunction with user I/O devices that are capable of providing information to, and receiving information and commands from, a user.

In some embodiments, analysis circuit 126 may be installed local to platform 800, as shown in the example embodiment of FIG. 8. Alternatively, platform 800 can be implemented in a client-server arrangement wherein at least some functionality associated with these circuits is provided to platform 800 using an applet, such as a JavaScript applet, or other downloadable module. Such a remotely accessible module or sub-module can be provisioned in real-time, in response to a request from a client computing system for access to a given server having resources that are of interest to the user of the client computing system. In such embodiments the server can be local to network 894 or remotely coupled to network 894 by one or more other networks and/or communication channels. In some cases access to resources on a given network or computing system may require credentials such as usernames, passwords, and/or compliance with any other suitable security mechanism.

In various embodiments, platform 800 may be implemented as a wireless system, a wired system, or a combination of both. When implemented as a wireless system, platform 800 may include components and interfaces suitable for communicating over a wireless shared media, such as one or more antennae, transmitters, receivers, transceivers, amplifiers, filters, control logic, and so forth. An example of wireless shared media may include portions of a wireless spectrum, such as the radio frequency spectrum and so forth. When implemented as a wired system, platform 800 may include components and interfaces suitable for communicating over wired communications media, such as input/output adapters, physical connectors to connect the input/output adaptor with a corresponding wired communications medium, a network interface card (NIC), disc controller, video controller, audio controller, and so forth. Examples of wired communications media may include a wire, cable metal leads, printed circuit board (PCB), backplane, switch fabric, semiconductor material, twisted pair wire, coaxial cable, fiber optics, and so forth.

Various embodiments may be implemented using hardware elements, software elements, or a combination of both. Examples of hardware elements may include processors, microprocessors, circuits, circuit elements (for example, transistors, resistors, capacitors, inductors, and so forth), integrated circuits, ASICs, programmable logic devices, digital signal processors, FPGAs, logic gates, registers, semiconductor devices, chips, microchips, chipsets, and so forth. Examples of software may include software components, programs, applications, computer programs, application programs, system programs, machine programs, operating system software, middleware, firmware, software modules, routines, subroutines, functions, methods, procedures, software interfaces, application program interfaces, instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power level, heat tolerances, processing cycle budget, input data rates, output data rates, memory resources, data bus speeds, and other design or performance constraints.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still cooperate or interact with each other.

The various embodiments disclosed herein can be implemented in various forms of hardware, software, firmware, and/or special purpose processors. For example, in one embodiment at least one non-transitory computer readable storage medium has instructions encoded thereon that, when executed by one or more processors, cause one or more of the methodologies disclosed herein to be implemented. The instructions can be encoded using a suitable programming language, such as C, C++, object oriented C, Java, JavaScript, Visual Basic .NET, Beginner's All-Purpose Symbolic Instruction Code (BASIC), or alternatively, using custom or proprietary instruction sets. The instructions can be provided in the form of one or more computer software applications and/or applets that are tangibly embodied on a memory device, and that can be executed by a computer having any suitable architecture. In one embodiment, the system can be hosted on a given website and implemented, for example, using JavaScript or another suitable browser-based technology. For instance, in certain embodiments, the system may leverage processing resources provided by a remote computer system accessible via network 894. The computer software applications disclosed herein may include any number of different modules, sub-modules, or other components of distinct functionality, and can provide information to, or receive information from, still other components. These modules can be used, for example, to communicate with input and/or output devices such as a display screen, a touch sensitive surface, a printer, and/or any other suitable device. Other componentry and functionality not reflected in the illustrations will be apparent in light of this disclosure, and it will be appreciated that other embodiments are not limited to any particular hardware or software configuration. Thus in other embodiments platform 800 may comprise additional, fewer, or alternative subcomponents as compared to those included in the example embodiment of FIG. 8.

The aforementioned non-transitory computer readable medium may be any suitable medium for storing digital information, such as a hard drive, a server, a flash memory, and/or random access memory (RAM), or a combination of memories. In alternative embodiments, the components and/or modules disclosed herein can be implemented with hardware, including gate level logic such as a field-programmable gate array (FPGA), or alternatively, a purpose-built semiconductor such as an application-specific integrated circuit (ASIC). Still other embodiments may be implemented with a microcontroller having a number of input/output ports for receiving and outputting data, and a number of embedded routines for carrying out the various functionalities disclosed herein. It will be apparent that any suitable combination of hardware, software, and firmware can be used, and that other embodiments are not limited to any particular system architecture.

Some embodiments may be implemented, for example, using a machine readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, process, or the like, and may be implemented using any suitable combination of hardware and/or software. The machine readable medium or article may include, for example, any suitable type of memory unit, memory device, memory article, memory medium, storage device, storage article, storage medium, and/or storage unit, such as memory, removable or non-removable media, erasable or non-erasable media, writeable or rewriteable media, digital or analog media, hard disk, floppy disk, compact disk read only memory (CD-ROM), compact disk recordable (CD-R) memory, compact disk rewriteable (CR-RW) memory, optical disk, magnetic media, magneto-optical media, removable memory cards or disks, various types of digital versatile disk (DVD), a tape, a cassette, or the like. The instructions may include any suitable type of code, such as source code, compiled code, interpreted code, executable code, static code, dynamic code, encrypted code, and the like, implemented using any suitable high level, low level, object oriented, visual, compiled, and/or interpreted programming language.

Unless specifically stated otherwise, it may be appreciated that terms such as "processing," "computing," "calculating," "determining," or the like refer to the action and/or process of a computer or computing system, or similar electronic computing device, that manipulates and/or transforms data represented as physical quantities (for example, electronic) within the registers and/or memory units of the computer system into other data similarly represented as physical quantities within the registers, memory units, or other such information storage transmission or displays of the computer system. The embodiments are not limited in this context.

The terms "circuit" or "circuitry," as used in any embodiment herein, are functional and may comprise, for example, singly or in any combination, hardwired circuitry, programmable circuitry such as computer processors comprising one or more individual instruction processing cores, state machine circuitry, and/or firmware that stores instructions executed by programmable circuitry. The circuitry may include a processor and/or controller configured to execute one or more instructions to perform one or more operations described herein. The instructions may be embodied as, for example, an application, software, firmware, etc. configured to cause the circuitry to perform any of the aforementioned operations. Software may be embodied as a software package, code, instructions, instruction sets and/or data recorded on a computer-readable storage device. Software may be embodied or implemented to include any number of processes, and processes, in turn, may be embodied or implemented to include any number of threads, etc., in a hierarchical fashion. Firmware may be embodied as code, instructions or instruction sets and/or data that are hard-coded (e.g., nonvolatile) in memory devices. The circuitry may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Other embodiments may be implemented as software executed by a programmable control device. In such cases, the terms "circuit" or "circuitry" are intended to include a combination of software and hardware such as a programmable control device or a processor capable of executing the software. As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Numerous specific details have been set forth herein to provide a thorough understanding of the embodiments. It will be understood by an ordinarily-skilled artisan, however, that the embodiments may be practiced without these specific details. In other instances, well known operations, components and circuits have not been described in detail so as not to obscure the embodiments. It can be appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments

The following examples pertain to further embodiments, from which numerous permutations and configurations will be apparent.

Example 1 is a method for monitoring anatomical stress. The method comprises: receiving a plurality of pressure measurement samples associated with anatomical stress locations of a subject; calculating a percentage of the samples that exceed a threshold pressure value during a selected time period; determining an alert condition associated with the calculated percentage exceeding a percentage threshold value; and generating a notification message, in response to the determination of the alert condition.

Example 2 includes the subject matter of Example 1, further comprising storing each of the plurality of pressure measurement samples in a first-in-first-out (FIFO) buffer, wherein a size of the FIFO and a sampling rate for the pressure measurements are chosen to match the selected time period.

Example 3 includes the subject matter of Examples 1 or 2, further comprising maintaining statistics associated with frequency of occurrence and durations of the alert condition.

Example 4 includes the subject matter of any of Examples 1-3, further comprising transmitting the notifications to a mobile device over a wireless communications link.

Example 5 includes the subject matter of any of Examples 1-4, wherein the wireless communications link comprises Bluetooth communications.

Example 6 includes the subject matter of any of Examples 1-5, wherein the anatomical stress locations comprise one or more of the subject's knees, the subject's feet, and the subject's back.

Example 7 includes the subject matter of any of Examples 1-6, wherein the pressure measurement samples are received from a force sensitive resistor.

Example 8 is an apparatus for monitoring anatomical stress. The apparatus comprises: a pressure measurement circuit to provide a plurality of pressure measurement samples associated with anatomical stress locations of a subject; and an analysis circuit to: calculate a percentage of the samples that exceed a threshold pressure value during a selected time period; determine an alert condition associated with the calculated percentage exceeding a percentage threshold value; and generate a notification message, in response to the determination of the alert condition.

Example 9 includes the subject matter of Example 8, further comprising a memory circuit to store each of the plurality of pressure measurement samples in a first-in-first-out (FIFO) buffer, wherein a size of the FIFO and a sampling rate for the pressure measurements are chosen to match the selected time period.

Example 10 includes the subject matter of Examples 8 or 9, wherein the analysis circuit is further to maintain statistics associated with frequency of occurrence and durations of the alert condition.

Example 11 includes the subject matter of any of Examples 8-10, further comprising a communications circuit to transmit the notifications to a mobile device over a wireless communications link.

Example 12 includes the subject matter of any of Examples 8-11, wherein the wireless communications link comprises Bluetooth communications.

Example 13 includes the subject matter of any of Examples 8-12, wherein the anatomical stress locations comprise one or more of the subject's knees, the subject's feet, and the subject's back.

Example 14 includes the subject matter of any of Examples 8-13, wherein the pressure measurement circuit further comprises a force sensitive resistor to generate the pressure measurement samples.

Example 15 includes the subject matter of any of Examples 8-14, wherein the apparatus is integrated into a wearable device.

Example 16 includes the subject matter of any of Examples 8-15, wherein the wearable device is one of a knee pad, a type of footwear, or a backrest.

Example 17 is at least one non-transitory computer readable storage medium having instructions encoded thereon that, when executed by one or more processors, result in the following operations for monitoring anatomical stress. The operations comprise: receiving a plurality of pressure measurement samples associated with anatomical stress locations of a subject; calculating a percentage of the samples that exceed a threshold pressure value during a selected time period; determining an alert condition associated with the calculated percentage exceeding a percentage threshold value; and generating a notification message, in response to the determination of the alert condition.

Example 18 includes the subject matter of Example 17, the operations further comprising storing each of the plurality of pressure measurement samples in a first-in-first-out (FIFO) buffer, wherein a size of the FIFO and a sampling rate for the pressure measurements are chosen to match the selected time period.

Example 19 includes the subject matter of Examples 17 or 18, the operations further comprising maintaining statistics associated with frequency of occurrence and durations of the alert condition.

Example 20 includes the subject matter of any of Examples 17-19, the operations further comprising transmitting the notifications to a mobile device over a wireless communications link.

Example 21 includes the subject matter of any of Examples 17-20, wherein the anatomical stress locations comprise one or more of the subject's knees, the subject's feet, and the subject's back; and the pressure measurement samples are received from a force sensitive resistor.

Example 22 is a method for monitoring anatomical stress. The method comprises: receiving notification messages from a user-wearable device, the messages associated with anatomical stress pressure measurements of the user that exceed threshold frequency and duration values; generating alerts to the user, based on the notification messages; determining an identification of the user; and transmitting the notification messages and the user identification to a cloud-based analysis system.

Example 23 includes the subject matter of Example 22, further comprising selecting the frequency and duration threshold values and transmitting the frequency and duration threshold values to the user-wearable device.

Example 24 includes the subject matter of Examples 22 or 23, further comprising receiving statistics associated with the anatomical stress pressure measurements from the user-wearable device; and transmitting the statistics to the cloud-based analysis system.

Example 25 is a system for monitoring anatomical stress. The system comprises: means for receiving a plurality of pressure measurement samples associated with anatomical stress locations of a subject; means for calculating a percentage of the samples that exceed a threshold pressure value during a selected time period; means for determining an alert condition associated with the calculated percentage exceeding a percentage threshold value; and means for generating a notification message, in response to the determination of the alert condition.

Example 26 includes the subject matter of Example 25, further comprising means for storing each of the plurality of pressure measurement samples in a first-in-first-out (FIFO) buffer, wherein a size of the FIFO and a sampling rate for the pressure measurements are chosen to match the selected time period.

Example 27 includes the subject matter of Examples 25 or 26, further comprising means for maintaining statistics associated with frequency of occurrence and durations of the alert condition.

Example 28 includes the subject matter of any of Examples 25-27, further comprising means for transmitting the notifications to a mobile device over a wireless communications link.

Example 29 includes the subject matter of any of Examples 25-28, wherein the wireless communications link comprises Bluetooth communications.

Example 30 includes the subject matter of any of Examples 25-29, wherein the anatomical stress locations comprise one or more of the subject's knees, the subject's feet, and the subject's back.

Example 31 includes the subject matter of any of Examples 25-30, wherein the pressure measurement samples are received from a force sensitive resistor.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications. It is intended that the scope of the present disclosure be limited not be this detailed description, but rather by the claims appended hereto. Future filed applications claiming priority to this application may claim the disclosed subject matter in a different manner, and may generally include any set of one or more elements as variously disclosed or otherwise demonstrated herein.

What is claimed is:

1. A processor-implemented method for monitoring anatomical stress, the method comprising:
   receiving, by a processor, a plurality of pressure measurement samples associated with anatomical stress locations of a subject;
   calculating, by the processor, a percentage of the samples that exceed a threshold pressure value during a selected time period;
   determining, by the processor, an alert condition associated with the calculated percentage exceeding a percentage threshold value, wherein the threshold pressure value, the selected time period, and the percentage threshold value are chosen based on the anatomical stress location;
   reducing, by the processor, the percentage threshold value to a value less than 100% based on the anatomical stress location;
   generating, by the processor, a notification message, in response to the determination of the alert condition; and
   transmitting, by the processor, the notification message to a mobile device over a wireless communications link.

2. The method of claim 1, further comprising storing each of the plurality of pressure measurement samples in a first-in-first-out (FIFO) buffer, wherein a size of the FIFO and a sampling rate for the pressure measurements are chosen to match the selected time period.

3. The method of claim 1, further comprising maintaining statistics associated with frequency of occurrence and durations of the alert condition.

4. The method of claim 1, wherein the wireless communications link comprises Bluetooth communications.

5. The method of claim 1, wherein the anatomical stress locations comprise one or more of the subject's knees, the subject's feet, and the subject's back.

6. The method of claim 1, wherein the pressure measurement samples are received from a force sensitive resistor.

7. An apparatus for monitoring anatomical stress, the apparatus comprising:
   a pressure measurement circuit to provide a plurality of pressure measurement samples associated with anatomical stress locations of a subject; and
   an analysis circuit to: calculate a percentage of the samples that exceed a threshold pressure value during a selected time period; determine an alert condition associated with the calculated percentage exceeding a percentage threshold value; and generate a notification message, in response to the determination of the alert condition, wherein the threshold pressure value, the selected time period, and the percentage threshold value are chosen based on the anatomical stress location, and the percentage threshold value is reduced to a value less than 100% based on the anatomical stress location.

8. The apparatus of claim 7, further comprising a memory circuit to store each of the plurality of pressure measurement samples in a first-in-first-out (FIFO) buffer, wherein a size of the FIFO and a sampling rate for the pressure measurements are chosen to match the selected time period.

9. The apparatus of claim 7, wherein the analysis circuit is further to maintain statistics associated with frequency of occurrence and durations of the alert condition.

10. The apparatus of claim 7, further comprising a communications circuit to transmit the notifications to a mobile device over a wireless communications link.

11. The apparatus of claim 10, wherein the wireless communications link comprises Bluetooth communications.

12. The apparatus of claim 7, wherein the anatomical stress locations comprise one or more of the subject's knees, the subject's feet, and the subject's back.

13. The apparatus of claim 7, wherein the pressure measurement circuit further comprises a force sensitive resistor to generate the pressure measurement samples.

14. The apparatus of claim 7, wherein the apparatus is integrated into a wearable device.

15. The apparatus of claim 14, wherein the wearable device is one of a knee pad, a type of footwear, or a backrest.

16. At least one non-transitory computer readable storage medium having instructions encoded thereon that, when executed by one or more processors, result in the following operations for monitoring anatomical stress, the operations comprising:
   receiving a plurality of pressure measurement samples associated with anatomical stress locations of a subject;
   calculating a percentage of the samples that exceed a threshold pressure value during a selected time period;
   determining an alert condition associated with the calculated percentage exceeding a percentage threshold value, wherein the threshold pressure value, the selected time period, and the percentage threshold value are chosen based on the anatomical stress location;
   reducing, by the processor, the percentage threshold value to a value less than 100% based on the anatomical stress location;
   generating a notification message, in response to the determination of the alert condition; and
   transmitting the notification message to a mobile device over a wireless communications link.

17. The computer readable storage medium of claim 16, the operations further comprising storing each of the plurality of pressure measurement samples in a first-in-first-out (FIFO) buffer, wherein a size of the FIFO and a sampling rate for the pressure measurements are chosen to match the selected time period.

18. The computer readable storage medium of claim 16, the operations further comprising maintaining statistics associated with frequency of occurrence and durations of the alert condition.

19. The computer readable storage medium of claim 16, wherein the anatomical stress locations comprise one or more of the subject's knees, the subject's feet, and the subject's back; and the pressure measurement samples are received from a force sensitive resistor.

* * * * *